United States Patent [19]

Asfari et al.

[11] Patent Number: 5,902,577
[45] Date of Patent: May 11, 1999

[54] INSULIN-SECRETING CELL LINES, METHODS OF PRODUCTION AND USE

[75] Inventors: Maryam Asfari; Paul Czernichow, both of Paris, France

[73] Assignee: Merck Patent Gesellschaft mit beschrankter Haftung, Germany

[21] Appl. No.: 08/619,612

[22] PCT Filed: Sep. 27, 1994

[86] PCT No.: PCT/FR94/01129

§ 371 Date: Jun. 4, 1996

§ 102(e) Date: Jun. 4, 1996

[87] PCT Pub. No.: WO95/09231

PCT Pub. Date: Apr. 6, 1995

[30] Foreign Application Priority Data

Sep. 30, 1993 [FR] France .................................. 93/11687

[51] Int. Cl.[6] .......................... A61K 35/55; C12P 21/02; C12N 15/63; C27H 21/04
[52] U.S. Cl. ........................ 424/93.21; 424/424; 435/1.1; 435/69.4; 435/320.1; 435/353; 435/44; 435/385; 435/398; 435/284.1; 514/44; 530/303; 536/23.51
[58] Field of Search ................................. 424/93.21, 451, 424/490, 424; 435/69.1, 91.1, 172.3, 174, 240.22, 320.1, 101, 69.4, 284.1, 353, 382, 398; 514/3, 44; 530/303; 536/22.1, 23.51; 436/829

[56] References Cited

PUBLICATIONS

Inoue et. al.. Experimental hybrid islet transplantation: application of polyvinyl alcohol membrane for entrapment of islets. Pancreas vol. 7:562, Jul. 25, 1992.
deVos et. al.. Possible relationship between fibrotic overgrowth of algiinate–polylysine–alginate microencapsulated pancreatic islets and the microcapsule integrity. Transpl. Proc.. vol. 26(2):782–783, Apr. 12, 1994.
Seibers et. al.. Microencapsulated transplantation of allogeneic islets into specifically presensitized recipeints. Transpl. Proc.. vol.26(2):787–788, Apr. 12, 1994.
Mortensen et al., Production of Homozygous Mutant ES Cells With a Single Targeting Construct, Molecular and Cellular Biology, pp. 2391–2395, May 1992, vol. 12, No. 5.
Udy et al., "ES Cell Cycle Rates Affect Gene Targeting Frequencies," Experimental Cell Research 231, pp. 296–301, 1997.
Arbonés et al., "Gene Targeting in Normal Somatic Cells: Inactivation of the Interferon–γ Receptor in Myoblasts," Nature Genetics, vol. 6, pp. 90–96, Jan. 1994.

Scharp et al., "Protection of Encapsulated Human Islets Implanted Without Immunosuppression in Patients With Type I or Type II Diabetes and in Nondiabetic Control Subjects," Diabetes, vol. 43, pp. 1167–1170, Sep. 1994.
Sun et al., "Normalization of Diabetes in Spontaneously Diabetic Cynomolgus Monkeys by Xenografts of Microencapsulated Porcine Islets Without Immunosuppression," J. Clin. Invest., vol. 98, No. 6, pp. 1417–1422, Sep. 1996.
Monaco et al., "Islet Transplantation Using Immunoexclusion Methods," Transplantation Proceedings, vol. 28, No. 4, pp. 2042–2045, Aug. 1996.
Basta et al., "Method for Fabrication of Coherent Microcapsules: A New, Potential Immunoisolatory Barrier for Pancreatic Islet Transplantation," Diab. Nutr. Metab., vol. 8, No. 2, pp. 105–112, 1995.
Wang et al., "An Encapsulation System for the Immunosiolation of Pancreatic Islets," Nature Biotechnology, vol. 15, pp. 385–362, Apr. 1997.
Asfari et al., "Insulin–Like Growth Factor–II Gene Expression in a Rat Insulin–Producing Beta–Cell Line (INS–1) is Regulated by Glucose," Diabetologia, vol. 38, pp. 927–935, 1995.
Sandler et al., "Assessment of Insulin Secretion In Vitro From Microencapsulated Fetal Porcine Islet–Like Cell Clusters and Rat, Mouse, and Human Pancreatic Islets[1]," Transplantation, vol. 63, No. 12, pp. 1712–1718, Jun. 27, 1997.
Berinstein et al., "Gene Replacement With One–Sided Homologous Recombination," Molecular and Cellular Biology, vol. 12, No. 1, pp. 360–367, Jan. 1992.
DeChiara et al., "A Growth–Deficiency Phenotype in Heterozygous Mice Carrying an Insulin–Like Growth Factor II Gene Disrupted by Targeting," Nature, vol. 345, pp. 78–80, May 1990.
Shulman et al., "Homologus Recombination in Hybridoma Cells: Dependence on Time and Fragment Length," Molecular and Cellular Biology, vol. 10, No. 9, pp. 4466–4472, 1990.

Primary Examiner—James Ketter
Assistant Examiner—William Sandals
Attorney, Agent, or Firm—Millen, White, Zelano & Branigan, P.C.

[57] ABSTRACT

The invention relates to the field of biology and, in particular, to the field of cellular biology. The invention concerns a novel glucose-sensitive cell line designated β cell line (INS-I) expressing glucokinase and the glucose carrier Glut 2 at levels comparable with those of normal β cells but which is, in addition, incapable of IGF-II expression-dependent proliferation because of genetic manipulation. The invention also concerns a method for the production of said novel cell line, its aggregation in the form of a pseudoislet, its immobilization in a biocompatible hydrogel and its hardening by means of a hardening solution. Application in insulin-secreting β-cell transplants.

21 Claims, No Drawings

INSULIN-SECRETING CELL LINES, METHODS OF PRODUCTION AND USE

The present invention relates to the field of biology and, in particular, to the field of cell biology.

Its subject is in particular a novel cell line, capable of being implanted in a human organ so as to cause it to express the biological product which the novel cell line normally expresses in cultures.

The subject of the invention is specifically a novel glucose-sensitive cell line designated β cell line (INS-I) whose principal property is the sensitivity to glucose. These cells are therefore characterized by a high content of insulin, the possibility of expressing glucokinase and the glucose carrier Glut 2 at levels comparable with those of normal β cells and, in addition, these cells are made non-proliferating by genetic engineering.

This cell line is therefore capable of being transplanted into the organs of insulin-dependent subjects and of providing a "physiological" control of glycaemia in the case of insulin-dependent diabetes.

Organ transplant or tissue transplant forms part of the therapeutic tools used in a number of diseases. More recently, genetic engineering techniques have led to other possibilities being envisaged for the treatment of diseases which have up until now been incurable.

A research project is therefore proposed which combines transplantation and gene therapy for the treatment of diabetes mellitus. Indeed, the Applicants have established a β cell line, the INS-I line. This line secretes insulin in response to physiological concentrations of glucose and could, after genetic engineering, be used for transplantation and the "physiological" control of glycemia in insulin-dependent diabetes.

In spite of the therapeutic efforts which have been made in the last decade, the treatment of diabetes remains very unsatisfactory. That is the reason why novel therapies are explored; pancreas or islet transplants are a part thereof (Hellerstrom C, Andersson A, Groth C-G, Sandler S, Jansson L, Korsgren O, Swenne I, Petersson B, Tollemar J, Tydén G—Diabetes Care 11 (Suppl. 1) 45–53 1988) (Pipelleers D. G., Pipelleers-Marichal M, Hannaert J-C, Berghmans M, In't Veld P. A., Rozin J, Van de Winkel M, Gepts W—Diabetes 40:908–919 1991). More than a thousand whole pancreas transplants and a few tens of islet transplants have been performed worldwide. Although promising, these cumbersome techniques raise schematically two types of problem: some immunological, others logistical.

In addition to the problems of tolerance which are inherent to each type of transplant, it should be recalled that diabetes is an autoimmune disease and that the recipient, a diabetic, retains a potential to destroy the β cells transplanted. An absolute need therefore exists to combine an immunosuppressive therapy with the transplant. In order to avoid this immunosuppression, some authors have proposed the transplantation of encapsulated islets (Lacy P, Hegre O. D., Gerasimidi-Vazeo A, Gentile F. T., Dionne K. E.—Science 254:1782–1784 1991) (Chicheportich D, Reach G.—Diabetologia 31:54–57 1988). The essential advantage of the protection and especially of encapsulation is to protect the transplanted tissue from attack by the immune system. However, the low availability of islets makes the preparation of sufficient quantities of the material for therapeutic purposes difficult. Accordingly, considerable efforts have been devoted during the past ten years to establishing β cell lines as models for studying insulin secretion and diabetes. Most of these lines have lost their essential β cell function, namely the response to glucose by secretion of insulin, this loss occurring during subcultures and successive cell cycles. The Applicants have therefore been able to establish a highly differentiated β cell line (INS-I) whose characteristics are very similar to those of normal β cells (Asfari M, Janjic D, Meda P, Li G, Halban P. A., Wollheim C. B.—Endocrinology 130:167–178 1992) and this constitutes the essence of the invention.

Among the remarkable properties of these cells, there may be mentioned in particular the high insulin content, the expression of glucokinase, the glucose carrier Glut 2, at levels comparable to those of the normal β cell. Finally, the response to differentiation or growth factors such as growth hormone, prolactin IGF-I and IGF-II at physiological concentrations [sic]. The essential advantage of these cells is primarily their sensitivity to glucose. The Applicants have previously been able to show that an increase in glucose concentrations from 3 to 20 mM increases 4-fold the insulin secretion of INS-I cells in the presence of substances which increase the intracellular level of cAMP.

Recently, it has furthermore been shown that the incubation of these cells with physiological concentrations of glucose (48 h at 5 mM) makes them even more sensitive to variations in glucose concentration. These differentiation characteristics make these cells the most appropriate candidates for xenotransplantations in biocompatible capsules in diabetic subjects.

However, before the transplant, it is necessary to make these cells non-proliferating. Indeed, the inhibition of proliferation is essential if it is desired to avoid uncontrolled growth and a possible destruction of the protective capsule. This is obtained by destroying the genes involved (directly or indirectly) in the cell proliferation. It has recently been possible to show that IGF-II is abundantly expressed in these cells. IGF-II is a growth factor which modulates cell growth essentially in an autocrine manner. It is therefore possible to think, on the basis of recent results which are described later, that IGF-II is involved in the uncontrolled growth of these cells and that the inhibition of the expression of the IGF-II gene (by destroying the gene) is capable of inhibiting or of considerably reducing cell proliferation. By this genetic engineering, the INS-I cells would be capable of being adapted to encapsulation and to transplantation by making it possible to avoid any complications and difficulties leading to the preparation and the transplantation of pancreatic islets.

Finally, the proliferation of β cells, which are genetically modified and cultured in the absence of serum, is considerably reduced when the cells are cultured in the presence of a binding protein IGFBP-3 (Gopinath R, Walton P. E., Etherton E. D.—Endocrinol 120:231–236 1989). In the IGFBP-3 model, developed by the Applicants, sequestering IGF-II, its biological activity is reduced. The addition of IGFBP inhibits the proliferation of the INS-I cells. This observation suggests that IGF-II plays a major role in the proliferation of the INS-I cells because the only known function of the binding proteins (BP) and in particular of BP3, is to bind to the IGFs.

A number of indirect proofs support the results obtained: IGF-II stimulates cell proliferation in tumor lines in an autocrine-paracrine manner (El-Bardy O. H., Romanus J. A. I., Helman L. H., Cooper M. H., Rrchler M. M., Israel M. A.—J. Clin. Invest. 84:829 1989). This has also been demonstrated on transformed cells (Park J. H. Y., McCusker R. H., Vanderhoof J. A., Mohammadpour H, Harty R. F., MacDonald R. G.—Endocrinology 131:1359–1368 1992) and on primary β islet cultures (Rabinovith A, Quigley C, Russel T, Patel Y, Mintz D. H.—Diabetes 31:160–164 1982) (Hill D. J., Hogg J—E. M. Spencer (ed), Elsvier Science Publishing CO, INC 1991 235–240).

The subject of the invention is also the establishment of cell lines INS-I, which are genetically modified and encapsulated, with a view to their implantation.

PRELIMINARY RESULTS

These results relate essentially to the relationships between IGF-II, the glucose concentration in the culture medium and cell proliferation.

At 5 mM glucose, cell proliferation does not appear to be modified. From 5 mM up to 20 mM, an increase in proliferation is observed during periods ranging up to 72 h of culture. In parallel, an increase is observed in IGF-II messenger RNAs for glucose concentrations ranging from 10 to 20 mM.

It was not possible to detect either the IGF-I protein (radioimmunoassay) (Binoux M, Seurin D, Lassarre C, Gourmelen M.—J. Clin. Endocrinol. Metab. 59:453–462 1984), or its messenger RNA in these cells, even after long exposures to growth hormone.

PRINCIPLE OF THE METHOD

The work should be carried out in two stages:

establish a cell line INS-I which carries an inactive IGF-II gene, making the cells non-proliferating while maintaining their sensitivity to glucose encapsulation of these cells and transplantation into diabetic animals with the objective of subsequently performing transplants in man according to the same procedure.

EXPERIMENTAL PROCEDURE

Part I

The permanent inactivation of the IGF-II gene was performed by the homologous recombination technique (Riete H, Maandag E. R., Clarke A, Hooper M, Berns A—Nature 384:649–651 1990) (Pennington S, Wilson J. H.—Proc. Natl. Acad. Sci. 88:9498–9502 1991). The Applicants have available the cloned IGF-II gene in the plasmid pUC 119 (Dr HOLTHUIZEN) (Holthuizen P, Van der Lee F. M., Ikejiri K, Yamamoto M, Sussenbach J. S.—Biochem Biophys. Acta 1087:341–343 1990). Among the four different types of messenger RNAs encoding IGF-II, the 3.6 kb messenger RNA is principally expressed in the INS-I cells. This messenger is transcribed using the P3 promoter (Matsuguchi T, Takahashi K, Ikejiri K, Ueno T, Endo H, Yamamoto M—Biochem Biophys Acta 1048:165–170 1990).

It is proposed to insert a cassette encoding the neomycin (neo) resistance gene under the control of the promoter of the CMV early genes, placed in phase in exon 4 of the IGF-II gene. Downstream of this construct, a cassette encoding the herpes simplex virus thymidine kinase will be inserted. This construct makes it possible to select the rare clones having the IGF-II-neo construct by homologous recombination and not by random insertion. Indeed, the clones due to a homologous recombination will be resistant to neomycin and to gancyclovir whereas the clones due to a random recombination will be neomycin-resistant but gancyclovir sensitive.

The cells, after transfection, are cultured in the presence of neomycin, gancyclovir and IGF-II. The resistant clones are tested for their capacity to proliferate in the absence of endogenous IGF-II but in the presence of exogenous IGF-II and will be studied by the Southern blot technique and analysed by PCR with the aim of checking if the integration was correct. The expression of IGF-II will be studied at the level of the messenger RNAs and the proteins by the Northern and Western blot techniques respectively. Since it is established that only the paternal allel of the IGF-II gene is active (De Chaiara T. M., Robertson E. J., Efstratiadis A—Cell 64:849–859 1991), and since homologous recombination is more efficient at the level of the DNA segments which are transcriptionally active (Nickoloff J.C.—MEB 12:5311–5318 1992), it can be expected to obtain INS-I cells no longer expressing IGF-II by a single transfection/selection step. However, if this was not the case, the destruction of the second copy of the IGF-II gene may be undertaken (Riete H, Maandag E. R., Clarke A, Hooper M, Berns A.— Nature 384:649–651 1990). At each stage of this work, the ability of glucose to induce the secretion of insulin should be checked.

Part II

If the destruction (knock-out) of the IGF-II gene is successful, an INS-I cell line should finally be obtained which will be completely or to a large extent dependent on the exogenous administration of IGF-II for its growth. In theory, this new cell line will be sensitive to glucose in the same manner as the parental line. In this case, these cells can then therefore be used for the encapsulation and the transplantation.

1. Encapsulation of the INS-I cell line
    a) for an efficient encapsulation, the cells should be made into aggregates in a "pseudoislet" form. This can be performed by culturing the cells in nonadhesive culture dishes. The size of the aggregates (="pseudoislets") can be determined by the density of the cells at the time of the culture. On the other hand, the number of cells in the aggregates can be checked after trypsination of the "pseudoislets" (PI) harvested.
    b) a known number of PIs containing a quantity of insulin equivalent to that found in 500–1,000 adult rat islets ($2–4 \times 10^8$ cells) is suspended in a solution of sodium alginate (Lacy P, Hegre O. D., Gerasimidi-Vazeo A, Gentile F. T., Dionne K. E.—Science 254:1782–1784 1991) (Lanza R. P., Butler D. H., Borland K. M., Staruk J. E., Faustman D. L., Solomon B. A., Muller T. E., Rupp R. G., Maki T, Monaco A. P., Chick W. L.—Proc. Natl. Acad. Sci. 88:11100–11104 1991) and immobilized by encapsulation in this biocompatible hydrogel using an aqueous solution of a calcium salt. The PIs encapsulated will then be placed in tubular acrylic membranes which are permeable to molecules with a molecular weight of less than 50,000–80,000 (Lacy P, Hegre O. D., Gerasimidi-Vazeo A, Gentile F. T., Dionne K. E.— Science 254:1782–1784 1991) (Lanza R. P., Butler D. H., Borland K. M., Staruk J. E., Faustman D. L., Solomon B. A., Muller T. E., Rupp R. G., Maki T, Monaco A. P., Chick W. L.—Proc. Natl. Acad. Sci. 88:11100–11104 1991).
    c) the encapsulated PIs are studied "in vitro" by perifusion in order to determine the intensity and the speed at which they cause a change in insulin secretion in response to various glucose concentrations. When this part of the experiment is shown to be satisfactory, the PIs contained in fibers will be used for the transplantation.

2. Transplantation

The encapsulated PIs are transplanted subcutaneously or intraperitoneally. The two methods are efficient in maintaining normoglycemia in the animal models of human insulin-dependent diabetes. The biobreeding (BB) rats and the nonobese diabetic (NOD) mice which spontaneously develop diabetes are associated with a specific histocompatibility genotype and exhibit the same defects from the immunity point of view as the diabetic subjects (presence of cytotoxic T lymphocytes) of the diabetic animals who have undergone transplants (Lacy P, Hegre O. D., Gerasimidi-Vazeo A, Gentile F. T., Dionne K. E.—Science 254:1782–1784 1991) (Lanza R. P., Butler D. H., Borland K. M., Staruk J. E., Faustman D. L., Solomon B. A., Muller T. E., Rupp R. G., Maki T, Monaco A. P., Chick W. L.—Proc. Natl. Acad. Sci. 88:11100–11104 1991). The transplantation via the intraperitoneal route appears more favorable for ensuring a good biological environment for the transplanted cells.

This technique is applicable in the same manner to the insulin-dependent subjects. Between 50,000 and 200,000 PIs should be implanted in order to reach an effective insulin concentration.

We claim:

1. A highly differentiated insulin-secreting β-cell line comprising transformed β-cells, wherein said β-cells express insulin in response to glucose, and wherein expression of the insulin-like growth factor II (IGF-II) gene in said β-cells is permanently inhibited.

2. A cell line of claim 1, wherein expression of the insulin-like growth factor II (IGF-II) gene in said β-cell line is completely repressed.

3. A β-cell line of claim 1, wherein the endogenous IGF-II gene is knocked out.

4. A β-cell line of claim 1, wherein the highly differentiated insulin-secreting β-cell line is an INS-1 cell line.

5. A β-cell line of claim 1, wherein said β-cell line is in the form of pseudoislet aggregates.

6. A method of producing a transformed β-cell line of claim 1, comprising transfecting β-cells of a highly differentiated insulin-secreting β-cell line with a plasmid carrying a modified IGF-II gene, wherein said modified IGF-II gene has inserted, in phase in exon 4, a cassette encoding the neomycin resistance gene, and, downstream of said neomycin gene, a cassette encoding viral thymidine kinase, culturing said transfected β-cells in the presence of neomycin, gancyclovir and IGF-II, isolating transformed β-cells which are resistant to neomycin and gancyclovir, whereby transformed β-cells are obtained wherein said modified IGF-II gene has been incorporated by homologous recombination, whereby said β-cells are dependent on the exogenous administration of IGF-II for proliferation.

7. A method of claim 6, wherein the endogenous IGF-II gene is knocked out.

8. A method of claim 6, wherein the highly differentiated insulin-secreting β-cell line is an INS-I cell line.

9. A method of claim 6, wherein the plasmid is derived from pUC 119.

10. A method of claim 6, wherein the thus-produced β-cell line is further made into aggregates in the form of pseudoislets by culturing of the cells in nonadhesive culture dishes.

11. A method of claim 10, wherein the pseudoislets are agglomerated in suspension in a gelling agent and immobilized in a biocompatible hydrogel by adding an immobilizing agent.

12. A method of claim 11, wherein the gelling agent is a sodium alginate.

13. A method of claim 11, wherein the immobilizing agent is an aqueous solution of a calcium salt.

14. A method of claim 11, wherein the agglomerated and immobilized pseudoislets contain a quantity of insulin equivalent to that found in 500 to 1,000 islets in adult rats.

15. A method of claim 11, wherein the pseudoislets immobilized by encapsulation in a biocompatible hydrogel which has been hardened by adding an aqueous solution of a calcium salt are then placed in tubular acrylic membranes which are permeable to molecules with a molecular weight of less than 50,000–80,000.

16. A method of claim 15, wherein the immobilized and hardened pseudoislets are incorporated into transplantable fibers.

17. A biocompatible transplantable device, comprising pseudoislets of a transformed insulin-secreting β-cell line of claim 1, agglomerated and incorporated into tubular acrylic membranes which are permeable to molecules with a molecular weight of less than 50,000–80,000, and distributed in the form of fibers.

18. A transplantable device of claim 17, comprising 50,000 to 200,000 pseudoislets, whereby an effective amount of insulin for treating an insulin-dependent patient is produced.

19. A transplantable device of claim 17, adapted for transplant to a subcutaneous or intraperitoneal location.

20. A method of treating insulin deficiency in a patient in need of such treatment, comprising introducing into the body of said patient an effective amount of cells in the biocompatible transplantable device of claim 17.

21. A method of treating insulin deficiency in a patient in need of such treatment, comprising transplanting into the body of said patient a transplantable device of claim 17.

* * * * *